US011448577B2

(12) United States Patent
Liu et al.

(10) Patent No.: US 11,448,577 B2
(45) Date of Patent: Sep. 20, 2022

(54) SECOND-GENERATION IN-SITU TEST DEVICE FOR STRENGTH OF SHALLOW WATER SEDIMENT

(71) Applicant: Ocean University of China, Shandong (CN)

(72) Inventors: Xiaolei Liu, Shandong (CN); Hong Zhang, Shandong (CN); Yonggang Jia, Shandong (CN); Jiewen Zheng, Shandong (CN); Hongxian Shan, Shandong (CN)

(73) Assignee: Ocean University of China, Shandong (CN)

( * ) Notice: Subject to any disclaimer, the term of this patent is extended or adjusted under 35 U.S.C. 154(b) by 198 days.

(21) Appl. No.: 16/777,757

(22) Filed: Jan. 30, 2020

(65) Prior Publication Data

US 2020/0284709 A1 Sep. 10, 2020

(30) Foreign Application Priority Data

Mar. 6, 2019 (CN) .......................... 201910166966.5

(51) Int. Cl.
*G01N 3/06* (2006.01)
*G01N 33/24* (2006.01)
(Continued)

(52) U.S. Cl.
CPC ................ *G01N 3/10* (2013.01); *G01N 3/06* (2013.01); *B63B 35/00* (2013.01); *E02D 1/022* (2013.01);
(Continued)

(58) Field of Classification Search
CPC .. G01N 3/10; G01N 3/06; G01N 3/12; G01N 3/40; G01N 33/24; G01N 2203/026;
(Continued)

(56) References Cited

U.S. PATENT DOCUMENTS

| 6,257,165 B1 * | 7/2001 | Danos, Jr. ................. B63B 3/48 |
| | | 114/265 |
| 6,503,022 B1 * | 1/2003 | Nuss ....................... B63B 19/00 |
| | | 114/201 R |
| 11,110,997 B2 * | 9/2021 | Jia ............................. G01L 7/00 |

FOREIGN PATENT DOCUMENTS

| CN | 101838981 A | * | 9/2010 |
| CN | 102320347 A | * | 1/2012 |

(Continued)

*Primary Examiner* — Jonathan M Dunlap
(74) *Attorney, Agent, or Firm* — Berkeley Law & Technology Group, LLP

(57) ABSTRACT

The present invention discloses a second-generation in-situ test device for strength of a shallow water sediment, including a workboat and a static cone penetration test unit carried by the workboat, where the static cone penetration unit includes a mounting frame, a penetration unit, a control cabin and a hydraulic unit; the penetration unit and the hydraulic unit are both electrically connected to the control cabin. In this solution, the workboat is used to carry the test equipment, and the static cone penetration test unit is carried on the workboat with a special structure. Based on a double-cable lifting frame, the equipment is launched and recovered through a moon pool in the center of a hull. This significantly improves the efficiency and safety of the sediment strength test operation in a shallow water environment.

7 Claims, 4 Drawing Sheets

(51) Int. Cl.
*E02D 1/02* (2006.01)
*G01N 3/40* (2006.01)
*B63B 35/00* (2020.01)
*G01N 3/10* (2006.01)
*G01N 3/12* (2006.01)

(52) U.S. Cl.
CPC ............... *G01N 3/12* (2013.01); *G01N 3/40* (2013.01); *G01N 33/24* (2013.01); *G01N 2203/0019* (2013.01); *G01N 2203/0048* (2013.01); *G01N 2203/026* (2013.01)

(58) Field of Classification Search
CPC .... G01N 2203/0048; G01N 2203/0019; E02D 1/022; B63B 35/00
See application file for complete search history.

(56) References Cited

FOREIGN PATENT DOCUMENTS

| | | | | | |
|---|---|---|---|---|---|
| CN | 103144751 | A | * | 6/2013 | |
| CN | 106707361 | A | * | 5/2017 | |
| CN | 107000822 | A | * | 8/2017 | ............. B63B 35/03 |
| CN | 107632121 | A | * | 1/2018 | |
| CN | 107719591 | A | * | 2/2018 | |
| CN | 109094742 | A | * | 12/2018 | |
| CN | 110206007 | A | * | 9/2019 | |
| WO | WO-2019129068 | A1 | * | 7/2019 | ............. A01K 97/02 |

* cited by examiner

SECOND-GENERATION IN-SITU TEST DEVICE FOR STRENGTH OF SHALLOW WATER SEDIMENT

TECHNICAL FIELD

The present invention relates to the field of marine geological exploration, and in particular, to a second-generation in-situ test device for strength of a shallow water sediment.

BACKGROUND

Shallow waters mainly refer to coastal mudflats, intertidal zones, and sub-littoral zones with a depth of 20 m. Shallow water areas are not only important positions for China's petroleum exploration and development, but also strategic camps for the deployment of national coastal defense facilities. They have important scientific research, economic and military values. Therefore, it is especially important to accurately and quickly obtain the strength of the working area.

At present, sediment strength is usually tested by drilling to obtain a sample and carrying out an indoor test. The work cycle is long and the test accuracy is low. As an effective method to obtain sediment strength, static cone penetration test technology is widely used in land and ocean. However, the existing underwater static cone penetration test equipment involves large-volume and heavy instruments, which must be loaded with a large ship. Therefore, the existing underwater static cone penetration test equipment is only suitable for deep-sea submarine engineering geological investigation, and is rarely used in shallow water areas.

For example, an invention patent, with a publication number of CN101838981B, discloses an underwater rock-soil sounding device and an underwater rock-soil exploration method. This patent proposes an underwater rock-soil sounding device that can carry out rock-soil engineering survey in different scales of deep water and an underwater rock-soil exploration method using the device. The device and method solve the problem of poor transportability of cone penetration test equipment during the in-situ test of sea floor strength. However, the method involves large-volume and heavy equipment, which must be loaded with a large ship, so that the method is only suitable for deep-sea submarine engineering geological investigation. In addition, an invention patent, with a publication number of CN103144751B, discloses an original-space detector and detection method for beach shallow sea sediment strength. The device and method can realize the in-situ test of shallow water sediment strength. However, in specific work, the in-situ test equipment is towed by a boat in the water. The test equipment is independent of the boat and directly works on the water with the aid of a buoyancy generation device. This requires staff to control the operation of a probe rod on an upper part of the device, with poor safety.

SUMMARY

The present invention proposes a second-generation in-situ test device for strength of a shallow water sediment. The present invention aims to realize efficient, accurate and safe work in a shallow water area to obtain the strength of a sediment in the shallow water area. The present invention greatly reduces the number of boreholes in marine engineering investigation, and improves the quality and accuracy of engineering investigation. Besides, the present invention has obvious economic benefits, and greatly shortens the cycle of marine engineering geological evaluation and survey.

The present invention is implemented by using the following technical solution.

A second-generation in-situ test device for strength of a shallow water sediment includes a workboat and a static cone penetration test unit, where the workboat is used to freely navigate in a shallow water area, stand still on the sea after being anchored back and forth, and realize the carrying, launch, stabilization and recovery of the static cone penetration test unit; the workboat includes a hull, a moon pool and a lifting device; the moon pool is arranged on a foredeck of the hull, and the moon pool is provided with a cover plate for placing the static cone penetration test unit; the lifting device is arranged above the moon pool; the lifting device lifts with double cables, and is provided with a cable guide. The device can prevent equipment from rotating and limit the translation of the equipment passing through an opening of the moon pool.

The static cone penetration test unit is used to realize the test of sediment strength; the static cone penetration unit includes a mounting frame, a penetration unit, a control cabin and a hydraulic unit; the penetration unit and the hydraulic unit are electrically connected to the control cabin; the hydraulic unit powers the penetration unit; the penetration unit includes a probe rod and a probe rod lifting mechanism; the probe rod lifting mechanism is connected to the probe rod, and realizes the up and down movement of the probe rod under the control of the control cabin.

The probe rod lifting mechanism includes a pulley mechanism and a penetration cylinder; the pulley mechanism includes a lifting frame, a pulley block, and a transmission steel cable; the pulley block includes a first fixed pulley fixedly arranged on an upper part of the lifting frame, a second fixed pulley arranged on a lower part of the lifting frame, and two sets of movable pulleys arranged between the first fixed pulley and the second fixed pulley; a sliding chute is arranged on both sides of the lifting frame; the movable pulley can move up and down along the sliding chute; the first fixed pulley is connected to one set of movable pulleys through a first transmission steel cable, and the second fixed pulley is connected to the other set of movable pulleys through a second transmission steel cable.

The lifting frame is further provided with a slide rail and a guide plate sliding up and down along the slide rail; the guide plate is provided with an upper clamping cylinder; a lower clamping cylinder is arranged below the lifting frame; the upper clamping cylinder and the lower clamping cylinder are used to clamp the probe rod; one end of the first transmission steel cable is fixed, and the other end is connected to an upper side of the guide plate; one end of the second transmission steel cable is fixed, and the other end is connected to a lower side of the guide plate.

Further, the hull adopts a streamlined structure design, and includes a first underwater hull and a second underwater hull; the first underwater hull and the second underwater hull are symmetrically arranged along the length of the workboat from left to right; the first underwater hull and the second underwater hull are connected by a reinforced structure. The entire hull adopts a unique streamlined design. Upper parts of the two separated underwater hulls are connected by the reinforced structure to form a "catamaran structure" of the whole boat. In this way, the workboat has certain wind resistance, and can work normally in 3 to 9 degrees of sea state. In a tidal flat environment with a water depth less than 1 meters (m), the workboat can be towed by a trailer to a target point. If the water depth is greater than 1 m, a platform can be directly driven to the target point to carry out in-situ test of sediment strength.

Further, the hull is 20 m long and 6 m wide; the size of the middle moon pool is 2.2 m×2 m; the displacement of the workboat is 20 tons, and the draft is 1 m. The special design can meet the need of in-situ test in the shallow water.

Further, the number of the first fixed pulley, the second fixed pulley, and the movable pulley are two sets, respectively; the two sets of first fixed pulleys and the two sets of second fixed pulleys both are horizontally arranged; the two sets of movable pulleys are arranged up and down. The hydraulic drive and the pulleys are combined to form a stroke amplification mechanism, reducing the overall height of the equipment and improving the stability of the equipment on the sea floor. The maximum penetration depth can reach 20 m.

Further, the overall shape of the mounting frame is designed as a hexagonal prism frame structure; a side wall of the mounting frame is provided with a plurality of through holes; the overall height of the mounting frame is not greater than 1,500 mm. The mounting frame is more suitable for the special engineering geological environment of shallow waters to ensure the overall stability of the equipment.

Further, the mounting frame is correspondingly provided with a plurality of anchor rods at the bottom. The anchor rods penetrate into a sediment for fixing after the equipment descends to the sea floor. In this way, the mounting frame prevents the equipment from moving during operation. In order to facilitate lowering, the mounting frame is further provided with a lifting ring on the top; the lifting ring is used to connect a cable on a fixed gantry winch.

Further, the static cone penetration test unit further includes a control cabin and a sensor unit and a power battery compartment electrically connected to the control cabin; the sensor unit includes an attitude sensor for detecting a lowering attitude of the static cone penetration test unit, an altimeter, a displacement sensor for detecting a penetration state of the probe rod, and a pressure sensor; the power battery compartment is used to power the entire device.

Further, the mounting frame is further provided with a shooting and lighting device electrically connected to the control cabin; the shooting and lighting device includes a video camera and a lighting system; the angles of the video camera and the lighting system are adjustable.

Compared with the prior art, the present invention has the following advantages and positive effects.

In the present invention, the workboat is used to carry the test equipment, and the static cone penetration test equipment is carried on the workboat with a special structure. In this way, the present invention greatly improves the speed of the boat, and effectively improves the efficiency of a sediment strength test operation under a shallow water environment. Based on a double-cable lifting frame, the equipment is launched and recovered through the moon pool in the center of the hull. The connection and disassembly of some probe rods are completed on the cover plate of the moon pool, which further improves the safety of the static cone penetration test operation.

A stroke amplification mechanism combining a driving hydraulic cylinder and the pulley is designed in the lifting control of the probe rods. This reduces the overall height of the equipment, and improves the stability of the equipment on the sea floor, and the penetration depth can reach 20 m. Therefore, the in-situ test device can effectively improve the quality and accuracy of engineering investigation. Besides, the present invention has obvious economic benefits, and greatly shortens the cycle of marine engineering geological evaluation and survey.

DETAILED DESCRIPTION

To make the objectives, features and advantages of the present invention more comprehensible, the present invention is further described below with reference to the accompanying drawings and embodiments. It should be noted that the embodiments in the application and features in the embodiments may be combined with each other in a non-conflicting situation.

Figure 1:
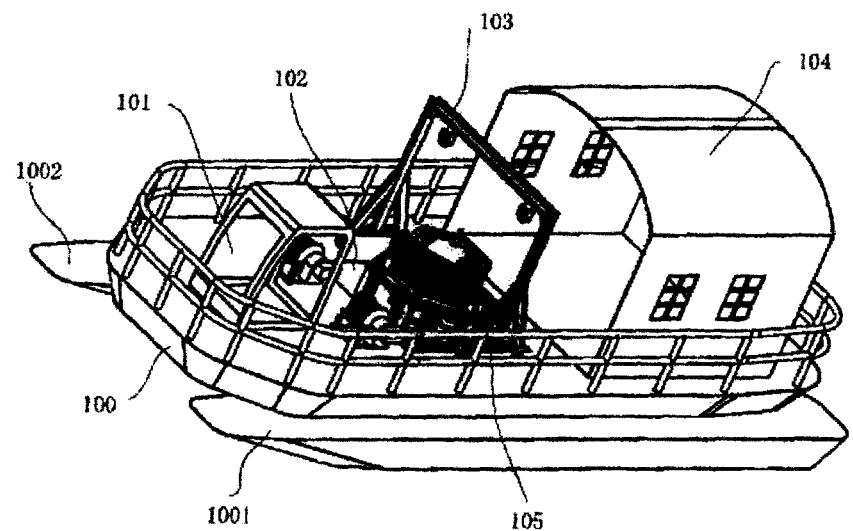
FIG. 1 is a schematic structural diagram of a workboat and a static cone penetration test unit according to an embodiment of the present invention.

A second-generation in-situ test device for strength of a shallow water sediment, as shown in FIG. 1, includes a workboat and a static cone penetration test unit. On the one hand, the workboat is used to freely navigate in a shallow water area. On the other hand, the workboat is used to carry, launch, stabilize and recover the static cone penetration test unit. The workboat can stand still on the sea after being anchored back and forth.

The workboat is a small catamaran boat, including a hull 100, a moon pool 102, a bridge 104, and a lifting device 103, etc. As can be seen from FIG. 1, the hull includes a first underwater hull 1001 and a second underwater hull 1002. The first underwater hull 1001 and the second underwater hull 1002 are symmetrically arranged along the length of the workboat from left to right. The first underwater hull 1001 and the second underwater hull 1002 are connected by a reinforced structure. The moon pool 102 is located on a foredeck of the hull, and is mainly used to place the static cone penetration test unit 105. The moon pool 102 is provided with a cover plate. The cover plat is opened when in use, and is closed when not in use. The lifting device 103 is arranged above the moon pool 102, and uses a fixed gantry winch. The lifting device lifts with double cables, and is provided with a cable guide. In this way, the lifting device can prevent equipment from rotating and limit the translation of the equipment passing through an opening of the moon pool. The lifting device has a lifting capacity of 2 tons. The hull is designed to be 20 m long, and 6 m wide, with a displacement of 20 tons, and a draft of 1 m. The workboat is able to stand still on the water after being anchored back and forth. The size of the middle moon pool is 2.2 m×2 m. An on-board generator of the workboat can provide 380 V/50 Hz, and no less than 8 kw of system power. A hull engine is a gasoline or diesel engine, with a design speed of 5 knots. The entire hull adopts a unique streamlined design. Upper parts of the two separated underwater hulls are connected by the reinforced structure to form a "catamaran structure" of the whole boat. In this way, the workboat has certain wind resistance, and can work normally in 3 to 9 degrees of sea state. In a tidal flat environment with a water depth less than 1 m, the workboat can be towed by a trailer to a target point to carry out in-situ test of sediment strength.

Figure 2:
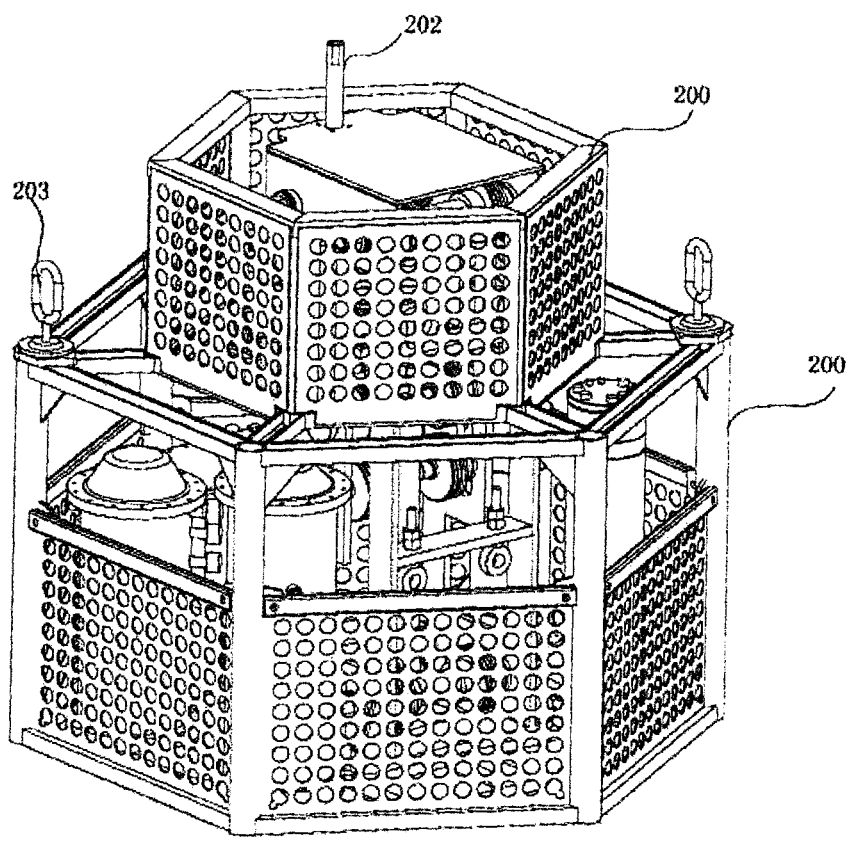
FIG. 2 is a schematic structural diagram of an entire static cone penetration test unit according to an embodiment of the present invention.
Figure 3:
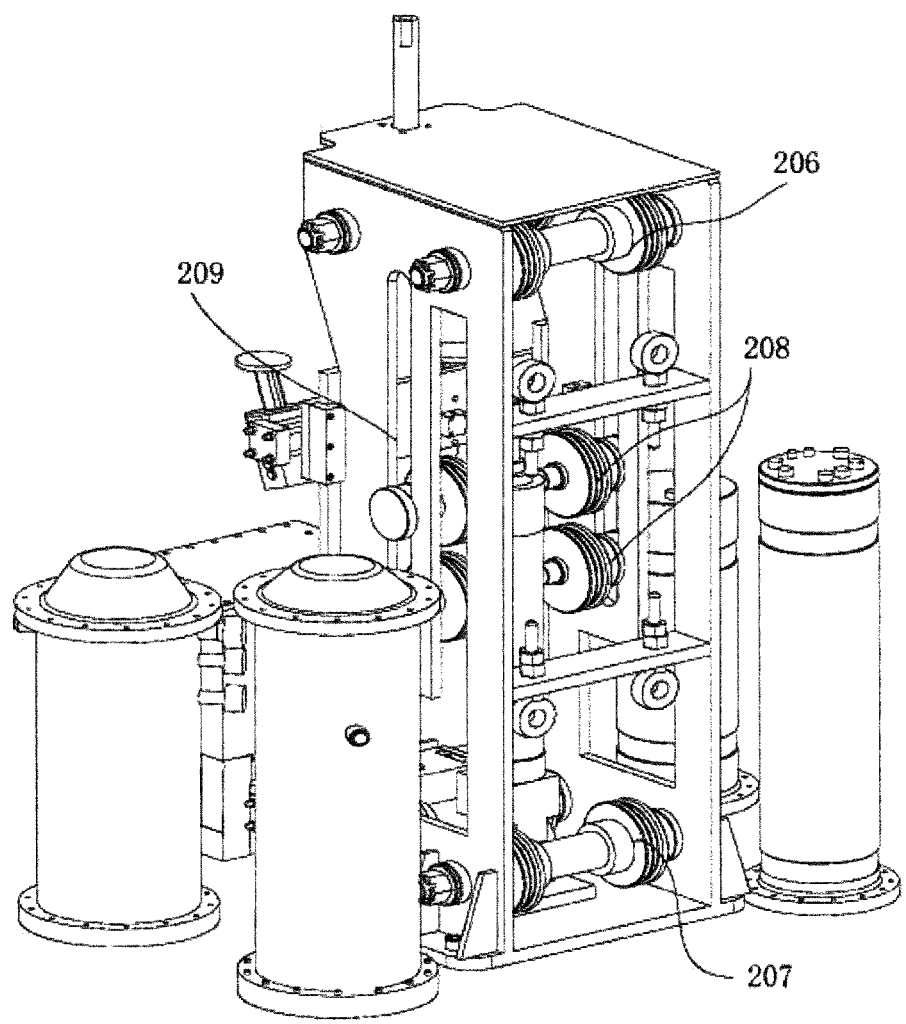
FIG. 3 is a front-view structural diagram of a static cone penetration test unit without a mounting frame in FIG. 2.
Figure 4:
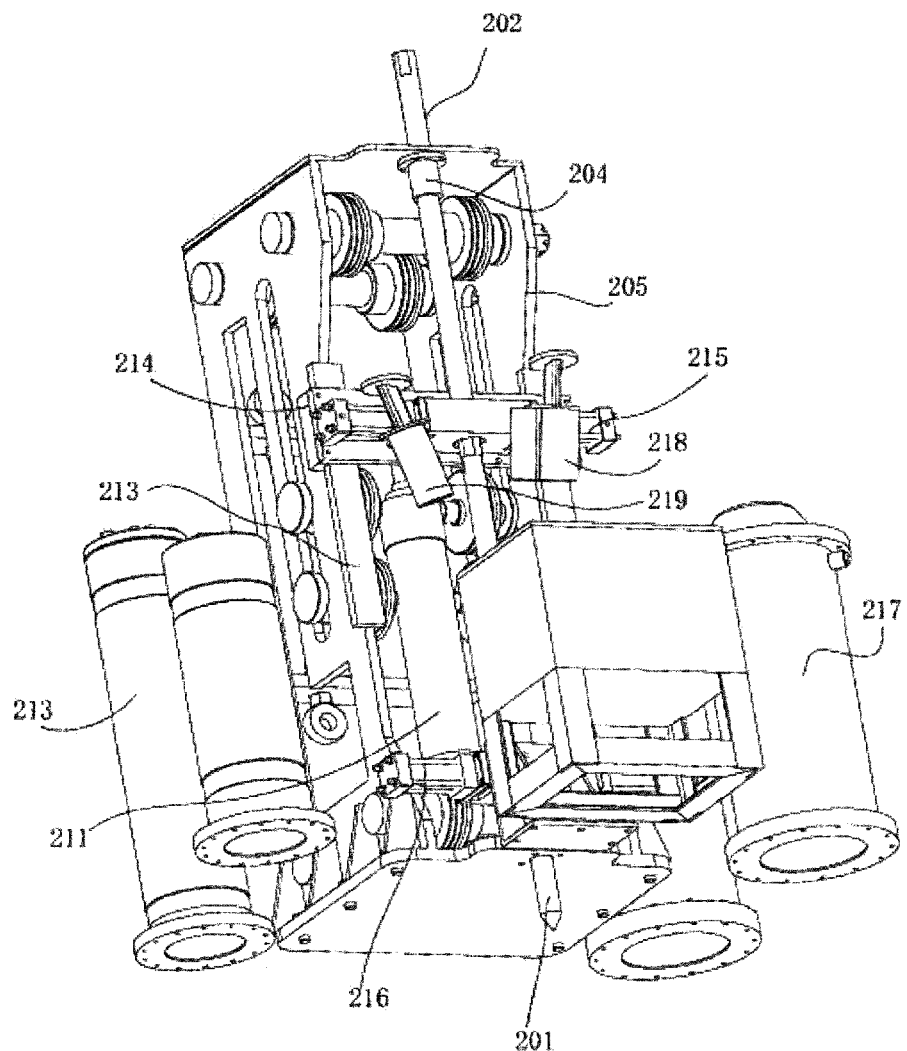
FIG. 4 is a rear-view structural diagram of a static cone penetration test unit without a mounting frame in FIG. 2.

The static cone penetration test unit is mainly used to test sediment strength. The static cone penetration unit includes a mounting frame 200, a penetration unit, a control cabin 213 and a hydraulic unit. The penetration unit and the hydraulic unit are electrically connected to the control cabin. The hydraulic unit powers the penetration unit. As shown in FIG. 2 to FIG. 4, the overall shape of the mounting frame 200 is designed as a hexagonal prism frame structure, so as to improve the stability of the frame of the device. The mounting frame 200 is further provided with a lifting ring 203 on the top, for connecting a cable on the fixed gantry winch. The mounting frame is correspondingly provided with 6 anchor rods (not show in the figure) on the bottom. After the equipment descends into the sea floor, the anchor rods penetrate into a sediment to prevent the equipment from moving during operation. According to the requirements of the equipment for the test depth and the structure of the control cabin, the hydraulic unit and other components, the size of the mounting frame is proposed to be designed as 1,740 millimeters (mm) (diagonal)×1,450 mm (opposite side), and the overall height is 1,500 mm. In addition, the mounting frame is further provided with a shooting and lighting device electrically connected to the control cabin. The shooting and lighting device includes a video camera 218 and a lighting system 219. The angles of the video camera and the lighting system are adjustable.

Referring to FIG. 3 and FIG. 4, the penetration unit includes a probe rod 202 and a probe rod lifting mechanism. A probe 201 is arranged below the probe roe 202. The probe rod lifting mechanism is connected to the probe rod 202, and realizes the up and down movement of the probe rod 202 under the control of the control cabin. The probe rod lifting mechanism includes a pulley mechanism and a penetration cylinder 211. The pulley mechanism includes a lifting frame 205, a pulley block, and a transmission steel cable. The probe rod is arranged on the lifting frame through a guide sleeve 204. The pulley block includes a first fixed pulley 206 fixedly arranged on an upper part of the lifting frame 205, a second fixed pulley 207 arranged on a lower part of the lifting frame 205, and two sets of movable pulleys 208 arranged between the first fixed pulley 206 and the second fixed pulley 207. A sliding chute 209 is arranged on both sides of the lifting frame 205. The movable pulley 208 can move up and down along the sliding chute 209. The first fixed pulley 206 is connected to one set of movable pulleys through a first transmission steel cable 210, and the second fixed pulley 207 is connected to the other set of movable pulleys through a second transmission steel cable (212).

The lifting frame 205 is further provided with a slide rail 213 and a guide plate 214 sliding up and down along the slide rail 213. The guide plate 214 is provided with an upper clamping cylinder 215. A lower clamping cylinder 216 is arranged below the lifting frame 205. The upper clamping cylinder 215 and the lower clamping cylinder 216 are used to clamp the probe rod 202. One end of the first transmission steel cable is fixed, and the other end is connected to an upper side of the guide plate 214. One end of the second transmission steel cable is fixed, and the other end is connected to a lower side of the guide plate 214.

Figure 5:
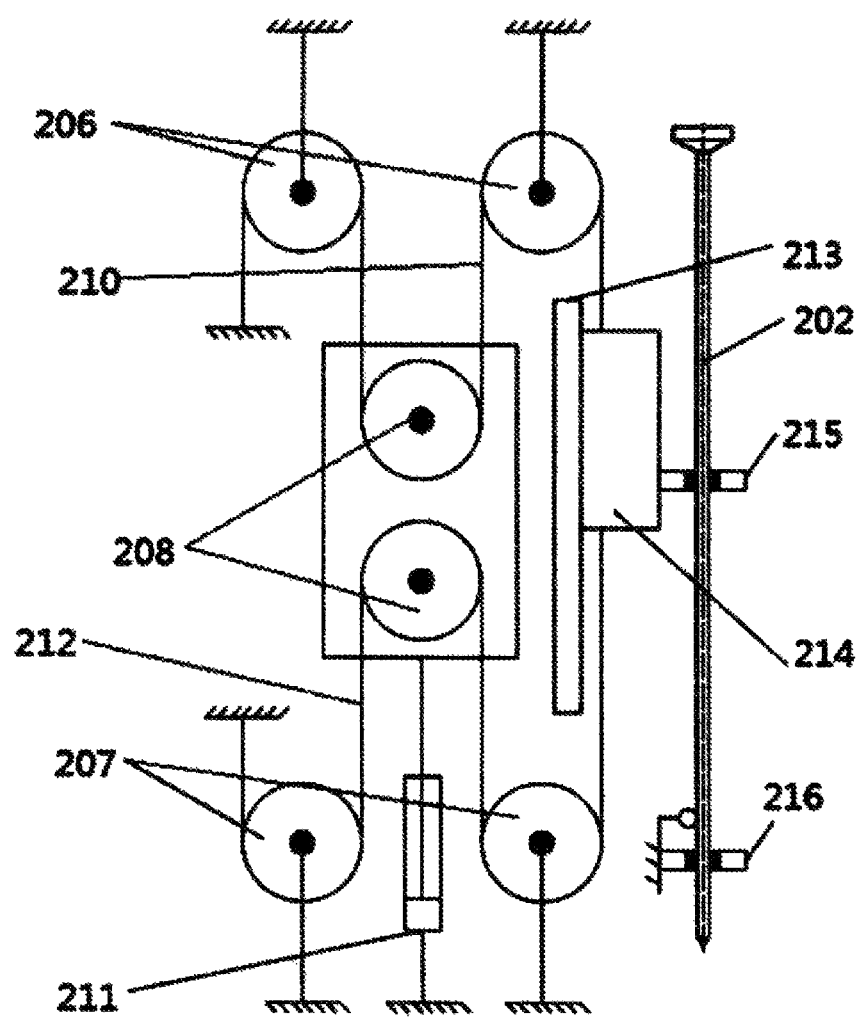
FIG. 5 is a schematic diagram of a probe rod lifting mechanism according to an embodiment of the present invention.

The working principle of the penetration unit is shown in FIG. 5. In this embodiment, the number of the first fixed pulley 206, the second fixed pulley 207, and the movable pulley 208 are two sets, respectively. The two sets of first fixed pulleys 206 and the two sets of second fixed pulleys 207 both are horizontally arranged. The two sets of movable pulleys 208 are arranged up and down. When the probe rod penetrates, a piston rod of the penetration cylinder is extended, and the guide plate is driven to move downward through the transmission steel cable and the entire pulley block. A clamping manipulator fixed on the guide plate drives the probe rod to slowly and uniformly insert into the sediment. The insertion depth is measured by the displacement sensor. When the probe rod is lifted, the piston rod of the cylinder is retracted, and the guide plate moves upward to lift the probe rod out of the sediment. The probe rod lifting mechanism uses a stroke amplification mechanism combining the driving hydraulic cylinder and the pulley. The probe rod lifting mechanism reduces the overall height of the equipment and improves the stability of the equipment on the sea floor.

The control cabin includes a pressure-resistant sealed cabin and a related control circuit. The control cabin is mainly used to control the up and down movement of the probe rod and power switching, and realize real-time communication of acquisition and control signals with a workboat deck display and control unit. The static cone penetration test unit further includes a sensor unit and a power battery compartment electrically connected to the control cabin. The sensor unit includes an attitude sensor for detecting a lowering attitude of the static cone penetration test unit, an altimeter, a displacement sensor for detecting a penetration state of the probe rod 202, and a pressure sensor. The power battery compartment is used to power the entire device. The sealed cabin adopts an appropriate pressure-resistant structure and sealing design to meet the functional requirements of different underwater pressure-resistant components. It adopts a pressure-compensated self-balanced design for the power battery compartment and a pressure-resistant shell-type carrying structure for underwater electronic equipment. The control circuit uses a microprocessor as an information processing control center. The control circuit connects a corresponding sensor and control object through a cable and a watertight connector. It completes the execution of an action instruction of an upper computer, and completes the acquisition, storage, and upload of underwater analog, digital, and frequency signals. This design uses embedded technology with an STM32F103 single-chip microcomputer as the core to complete the design of the underwater real-time measurement and control circuit.

The hydraulic unit is mainly used to realize the penetration of the anchor rod and the probe rod. The hydraulic unit includes a deep-water direct current motor and a hydraulic pump. The control cabin sends an instruction to control each solenoid valve to complete the work of the equipment. A system pressure measured by the pressure sensor of the hydraulic unit can be used to calculate a penetration force. A parameter measured by a displacement sensor of the penetration cylinder and a displacement sensor of the probe rod can be used to detect the insertion depth of the probe rod. When the probe rod is inserted to a set depth or working pressure, a deck control platform of the workboat analyzes and processes a currently detected parameter, and issues an instruction for a next operation until all work is completed.

In addition, in the present invention, the workboat and the static cone penetration test equipment may also adopt other structural forms of shape design. Those achieving the purpose of the present invention and completing the in-situ test of the sediment strength also belong to the protection scope of the patent of the present invention.

The above are only preferred embodiments of the present invention, and are not intended to limit the present invention in other forms. Any person skilled in the art may change or modify the technical content disclosed above into an equivalent embodiment to be applied in other fields. Any simple amendment or equivalent change and modification of the above embodiments made according to the technical essence of the present invention without departing from the content of the technical solution of the present invention shall fall within the protection scope of the technical solution of the present invention.

What is claimed is:

1. A second-generation in-situ test device for strength of a shallow water sediment, comprising a workboat and a static cone penetration test unit (105), wherein the workboat freely navigates in a shallow water area, stands still on the sea after being anchored back and forth, and realizes the carrying, launch, stabilization and recovery of the static cone penetration test unit (105); the workboat comprises a hull (100), a moon pool (102) and a lifting device (103); the moon pool (102) is arranged on a foredeck of the hull; the moon pool (102) is provided with a cover plate for placing the static cone penetration test unit (105); the lifting device (103) is arranged above the moon pool; the lifting device lifts with double cables, and is provided with a cable guide;

the static cone penetration test unit (105) is used to realize the test of sediment strength; the static cone penetration unit comprises a mounting frame (200), a penetration unit, a control cabin (213) and a hydraulic unit; the penetration unit and the hydraulic unit are electrically connected to the control cabin; the hydraulic unit powers the penetration unit; the penetration unit comprises a probe rod (202) and a probe rod lifting mechanism; the probe rod lifting mechanism is connected to the probe rod (202), and realizes the up and down movement of the probe rod (202) under the control of the control cabin;

the probe rod lifting mechanism comprises a pulley mechanism and a penetration cylinder (211); the pulley mechanism comprises a lifting frame (205), a pulley block, and a transmission steel cable; the pulley block comprises a first fixed pulley (206) fixedly arranged on an upper part of the lifting frame (205), a second fixed pulley (207) arranged on a lower part of the lifting frame (205), and two sets of movable pulleys (208) arranged between the first fixed pulley (206) and the second fixed pulley (207); a sliding chute (209) is arranged on both sides of the lifting frame (205); the movable pulleys (208) can move up and down along the sliding chute (209); the first fixed pulley (206) is connected to one set of movable pulleys through a first transmission steel cable (210), and the second fixed pulley (207) is connected to the other set of movable pulleys through a second transmission steel cable (212);

the lifting frame (205) is further provided with a slide rail (213) and a guide plate (214) sliding up and down along the slide rail (213); the guide plate (214) is provided with an upper clamping cylinder (215); a lower clamping cylinder (216) is arranged below the lifting frame (205); the upper clamping cylinder (215) and the lower clamping cylinder (216) are used to clamp the probe rod (202); one end of the first transmission steel cable is fixed, and the other end is connected to an upper side of the guide plate; one end of the second transmission steel cable is fixed, and the other end is connected to a lower side of the guide plate; and wherein the overall shape of the mounting frame (200) is designed as a hexagonal prism frame structure; a side wall of the mounting frame (200) is provided with a plurality of through holes; and the overall height of the mounting frame (200) is not greater than 1,500 millimeters (mm).

2. The second-generation in-situ test device for strength of a shallow water sediment according to claim 1, wherein the hull (100) adopts a streamlined structure design, and comprises a first underwater hull (1001) and a second underwater hull (1002); the first underwater hull (1001) and the second underwater hull (1002) are symmetrically arranged along the length of the workboat from left to right; and the first underwater hull (1001) and the second underwater hull (1002) are connected by a reinforced structure.

3. The second-generation in-situ test device for strength of a shallow water sediment according to claim 2, wherein the hull (100) is 20 meters (m) long and 6 m wide; the size of the middle moon pool (102) is 2.2 m×2 m; and the displacement of the workboat is 20 tons, and the draft is 1 m.

4. The second-generation in-situ test device for strength of a shallow water sediment according to claim 1, wherein the number of the first fixed pulley (206), the second fixed pulley (207), and the movable pulley (208) are two sets, respectively; the two sets of first fixed pulleys (206) and the two sets of second fixed pulleys (207) both are horizontally arranged; and the two sets of movable pulleys (208) are arranged up and down.

5. The second-generation in-situ test device for strength of a shallow water sediment according to claim 1, wherein the mounting frame (200) is correspondingly provided with a plurality of anchor rods at the bottom, for fixing the mounting frame after descending to the sea floor; and the mounting frame (200) is further provided with a lifting ring (203) on the top.

6. The second-generation in-situ test device for strength of a shallow water sediment according to claim 1, wherein the static cone penetration test unit (105) further comprises a sensor unit and a power battery compartment (217) electrically connected to the control cabin; the sensor unit comprises an attitude sensor for detecting a lowering attitude of the static cone penetration test unit, an altimeter, a displacement sensor for detecting a penetration state of the probe rod (202), and a pressure sensor; and the power battery compartment is used to power the entire second-generation in-situ test device.

7. The second-generation in-situ test device for strength of a shallow water sediment according to claim 1, wherein the mounting frame (200) is further provided with a shooting and lighting device electrically connected to the control cabin; the shooting and lighting device comprises a video camera (218) and a lighting system (219); and the angles of the video camera (218) and the lighting system (219) are adjustable.

* * * * *